US008136986B2

(12) United States Patent
Lane et al.

(10) Patent No.: US 8,136,986 B2
(45) Date of Patent: Mar. 20, 2012

(54) DISPOSABLE SPECULUM FOR MEDICAL THERMOMETER

(75) Inventors: John A. Lane, Weedsport, NY (US); Scott A. Martin, Warners, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 345 days.

(21) Appl. No.: 11/942,430

(22) Filed: Nov. 19, 2007

(65) Prior Publication Data
US 2008/0123717 A1    May 29, 2008

Related U.S. Application Data

(63) Continuation-in-part of application No. 10/897,455, filed on Jul. 23, 2004, now Pat. No. 7,354,399.

(60) Provisional application No. 60/490,566, filed on Jul. 28, 2003, provisional application No. 60/507,473, filed on Sep. 30, 2003, provisional application No. 60/543,858, filed on Feb. 11, 2004.

(51) Int. Cl.
*G01K 1/08* (2006.01)
*A61B 1/227* (2006.01)

(52) U.S. Cl. ........ 374/158; 374/209; 374/163; 374/183; 374/208; 600/184

(58) Field of Classification Search .................. 374/158, 374/209, 120, 121, 130, 128, 163, 183, 126; 600/474, 549, 184
See application file for complete search history.

(56) References Cited

U.S. PATENT DOCUMENTS

| 3,110,304 | A | * | 11/1963 | Hartman | 600/200 |
| 3,374,791 | A | * | 3/1968 | Westerman | 606/191 |
| 3,929,018 | A | * | 12/1975 | Turner | 374/158 |
| 4,380,998 | A | * | 4/1983 | Kieffer et al. | 600/200 |
| 4,662,360 | A | * | 5/1987 | O'Hara et al. | 600/200 |
| 4,784,149 | A | * | 11/1988 | Berman et al. | 600/474 |
| 5,066,142 | A | * | 11/1991 | DeFrank et al. | 374/208 |
| 5,176,630 | A | * | 1/1993 | Shilling et al. | 604/41 |
| 5,390,663 | A | * | 2/1995 | Schaefer | 600/200 |
| 5,403,286 | A | * | 4/1995 | Lockwood, Jr. | 604/110 |
| 5,411,032 | A | * | 5/1995 | Esseff et al. | 600/549 |
| 5,893,833 | A | | 4/1999 | Pompei et al. | |

(Continued)

FOREIGN PATENT DOCUMENTS
WO    9942760 A1    8/1999
(Continued)

OTHER PUBLICATIONS

International Search Report, mailed Mar. 10, 2009, PCT/US2008/073956 (4 pgs.).

(Continued)

*Primary Examiner* — Gail Verbitsky
(74) *Attorney, Agent, or Firm* — Roger P. Bonenfant

(57) ABSTRACT

A tip element that is capable of being removably attached to an infrared thermometer and includes an axisymetric body having a distal end and an open proximal end. A membrane is located at the distal end of the body that is formed of an infrared transparent material. At least one engagement mechanism is mounted along the proximal edge of the body that has an engagement surface that passes circumferentially about a portion of the proximal edge and which contains an integral rib that extends axially toward said distal end of said body.

20 Claims, 7 Drawing Sheets

U.S. PATENT DOCUMENTS

| | | | | |
|---|---|---|---|---|
| 5,968,458 | A * | 10/1999 | Shaikho | 422/300 |
| 6,053,875 | A * | 4/2000 | Rosenbaum et al. | 600/559 |
| 6,129,673 | A | 10/2000 | Fraden | |
| 6,142,934 | A | 11/2000 | Lagerway et al. | |
| 6,155,987 | A * | 12/2000 | Scherl | 600/562 |
| 6,224,256 | B1 * | 5/2001 | Bala | 374/158 |
| 6,332,090 | B1 * | 12/2001 | DeFrank et al. | 600/474 |
| 6,347,243 | B1 | 2/2002 | Fraden | |
| 6,367,973 | B2 * | 4/2002 | Yamaka | 374/158 |
| 6,383,133 | B1 * | 5/2002 | Jones | 600/200 |
| 6,390,671 | B1 | 5/2002 | Tseng | |
| 6,612,735 | B2 * | 9/2003 | Tomioka et al. | 374/121 |
| 6,751,497 | B2 | 6/2004 | Fraden | |
| 6,786,636 | B1 * | 9/2004 | Huang et al. | 374/158 |
| 6,789,936 | B1 * | 9/2004 | Kraus et al. | 374/121 |
| 7,037,083 | B2 | 5/2006 | O'Neil et al. | |
| 7,083,330 | B1 * | 8/2006 | Yao | 374/209 |
| 7,237,949 | B2 * | 7/2007 | Lantz et al. | 374/158 |
| 7,494,273 | B2 * | 2/2009 | Huang et al. | 374/158 |
| 7,585,108 | B2 * | 9/2009 | Chuang et al. | 374/158 |
| 2002/0085616 | A1 * | 7/2002 | Yu | 374/158 |
| 2002/0163955 | A1 * | 11/2002 | Yu | 374/208 |
| 2003/0179809 | A1 * | 9/2003 | Nakagawa et al. | 374/158 |
| 2005/0027168 | A1 | 2/2005 | Strom et al. | |
| 2005/0027169 | A1 | 2/2005 | Goldfain et al. | |
| 2005/0043588 | A1 | 2/2005 | Tsai | |
| 2006/0020176 | A1 | 1/2006 | Berall | |
| 2008/0123717 | A1 | 5/2008 | Lane et al. | |
| 2008/0203078 | A1 | 8/2008 | Huerter | |

FOREIGN PATENT DOCUMENTS

WO     WO 02/056756 A2     7/2002

OTHER PUBLICATIONS

U.S. Appl. No. 11/678,357, filed Feb. 23, 2007, Lane.
Supplementary European Search Report dated Oct. 27, 2010, EP 08798437.3, 7 pgs.

\* cited by examiner

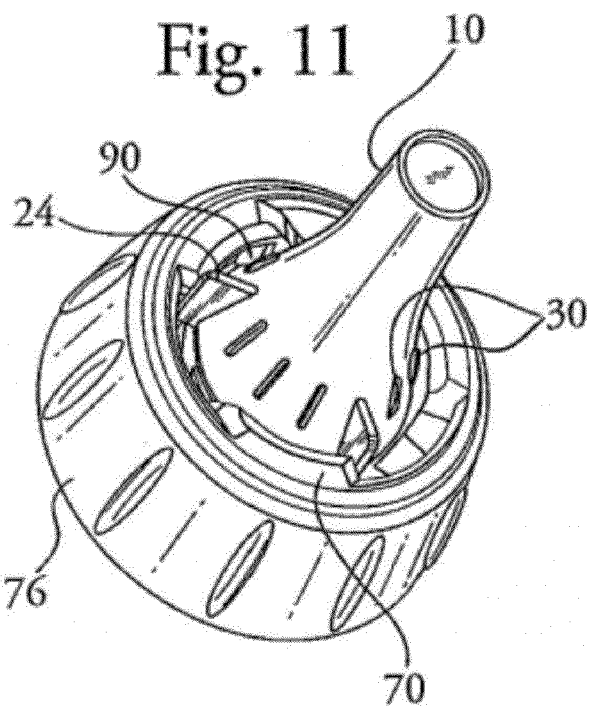
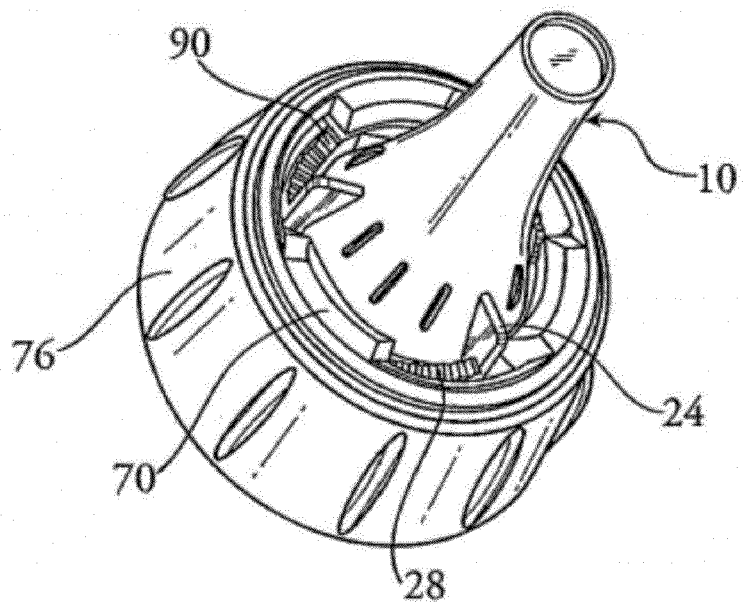

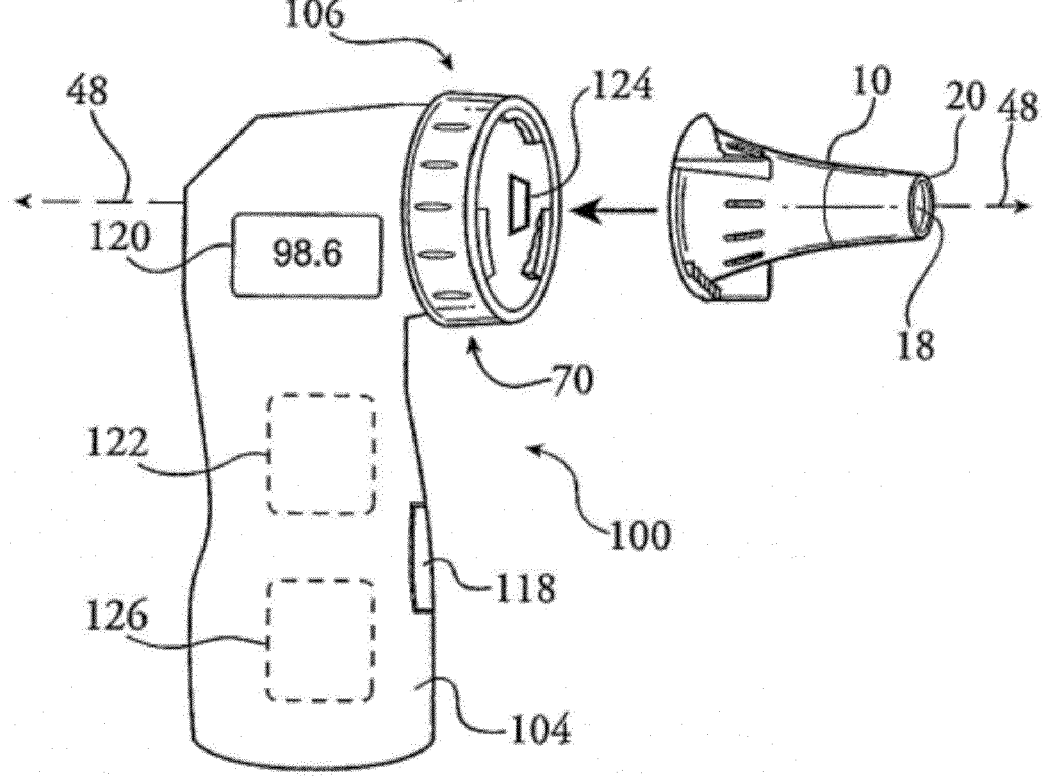

DISPOSABLE SPECULUM FOR MEDICAL THERMOMETER

CROSS-REFERENCE TO RELATED APPLICATIONS

This patent application is a continuation-in-part application under 37 C.F.R. 1.53(b) and claims benefit of priority under 35 U.S.C. 120 to commonly owned U.S. non-provisional patent application Ser. No. 10/897,455, filed Jul. 23, 2004, now U.S. Pat. No. 7,354,399 entitled "Otoscopic Tip Element and Related Method of Use", and which was published as U.S. Patent Publication No. 2005/0027168, and which claims priority under 35 U.S.C. 119(e) based upon the following commonly owned provisional patent applications: U.S. Ser. No. 60/543,858, filed Feb. 11, 2004, U.S. Ser. No. 60/507,473, filed Sep. 30, 2003 and U.S. Ser. No. 60/490,566, filed Jul. 28, 2003. All of the aforementioned patent(s) and patent application(s) are herein incorporated by reference in their entirety.

FIELD OF THE INVENTION

This invention relates generally to the field of temperature measurement, more particularly, to a disposable speculum which functions as a protective shield (cover) against contamination, for use with a medical thermometry apparatus.

BACKGROUND OF THE INVENTION

Some medical instruments are used for determining the body temperature of patients. These medical instruments typically employ a probe that includes at least one temperature sensitive element that is disposed within an interior cavity of the probe. The probe is inserted into a body site of interest, such as the axilla (arm pit), the mouth, the ear, the rectum, or other medical target of interest, and the body temperature is determined via an output of the temperature sensitive element, which can be implemented as a thermocouple, thermistor, thermopile, or other suitable type of transducer.

In order to prevent contamination between patients, a flexible speculum (protective shield) can be disposed onto the exterior of the probe. The speculum is typically a hollow plastic member that is typically injection molded to the desire configuration, however, other well known processes can be employed. Many of these devices also contain some type of latching mechanism for removably connecting the device to a medical instrument.

SUMMARY OF THE INVENTION

These and other objects, features, and advantages will become readily apparent from the following Detailed Description which should be read in conjunction with the accompanying drawings.

BRIEF DESCRIPTION OF THE DRAWINGS

The invention can be better understood with reference to the claims and drawings described below. The drawings are not necessarily to scale and the emphasis is instead generally being placed upon illustrating the principles of the invention. Within the drawings, like reference numbers are used to indicate like parts throughout the various views. Some differences between like parts may cause those parts to be indicated by different reference numbers. Unlike parts are indicated by different reference numbers.

FIG. 11 is a first partial front perspective view of a speculum attachment mechanism shown in an operative position;

FIG. 12 is a second partial front perspective view (showing teeth) of a speculum attachment mechanism shown in an operative position;

FIG. 13 is a side view of a speculum that is configured to attach to a medical thermometer according to one embodiment of the present invention.

DETAILED DESCRIPTION

The following describes a disposable speculum that is capable of being releasably connected to a medical thermometer. The speculum functions as a protective shield against contamination as well as enhancing the accuracy of the thermometer and aiding in the removal of cerum from the patients ear. However, from the description there are many variations and modifications that will become apparent to one of skill in the art that can be made in accordance with the following inventive aspects of the invention.

Figure 1:
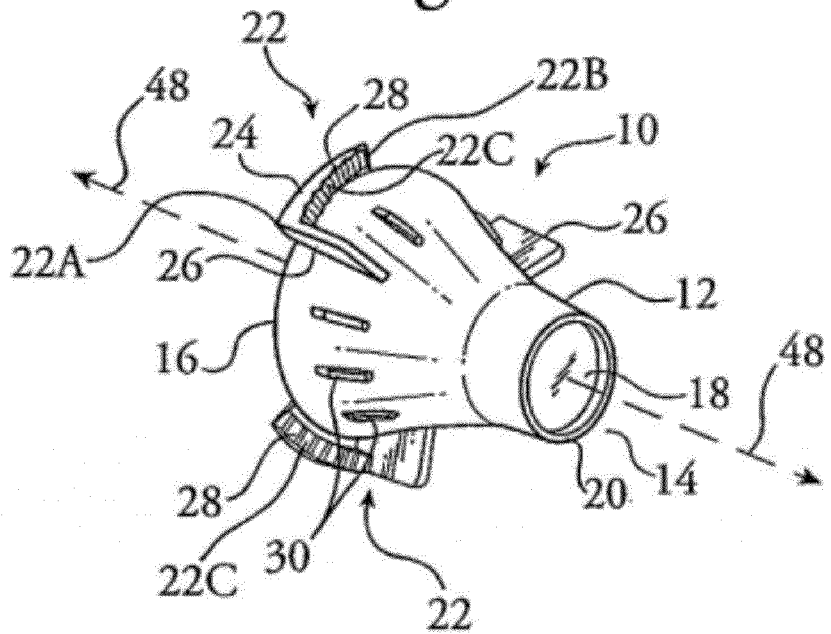
FIG. 1 is a perspective view of an embodiment of a disposable speculum for use in conjunction with a medical thermometer.

FIG. 1 is a perspective view of one embodiment of a speculum 10 for use in conjunction with a medical thermometer. As shown, the speculum 10 includes a generally tubular body 12, a distal end 14, and an open proximal end 16. A distal aperture 20 is located at the distal end 14. A membrane 18, which may be a radiation lens having high emissivity for gathering infrared radiation from the patients ear and directing the radiation onto a sensor that is located inside the instrument. The membrane is disposed at or near the distal aperture 20. As shown, the axis 48 of the speculum body is directed to intersect the membrane 18 at a substantially right angle and at a location that is substantially proximate to a center point of the membrane 18.

The speculum is configured to releasably attach to a medical thermometer 100 that includes an infrared sensor 124 (See FIG. 13). In some embodiments, the speculum 10 is injection molded from a plastic material such as polypropylene or polyethylene. It should be clear however that other suitable materials that are transparent to infrared radiation may be used while employing other fabrication procedures. The term transparent as herein used shall refer to a material that is capable of gathering radiation energy from its surrounding and concentrating the energy within a given plane.

In some embodiments, the speculum 10, regardless of the intended patient or site (e.g., pediatric, adult, etc.), includes a plurality of external engagement members 22 that are located in relation to the proximal open end 16 of the speculum. As shown, the proximal end 16 of the speculum 10 includes a plurality of external engagement members 22. In some embodiments, the engagement members 22 are designed to be disposed symmetrically, and in other embodiments the engagement members 22 are designed to be disposed asymmetrically, around an outer periphery at the proximal end 16 of the speculum body 12.

Further in accordance with the present embodiment, each engagement member 22 is disposed along the proximal edge of the speculum body 12. The engagement member is an L-shaped structure having an axially disposed rib 26 that forms a right angle corner 22(a) with a circumferentially disposed locking lug 24. The locking lug is wedged shaped so that its tip surface tapers downwardly from the corner toward its terminal edge 22(b). In addition, the two opposed side faces of the lug also taper towards one another from the corner toward the terminal edge. The inner side wall 22(c) of the lug may also contain a series of teeth 28.

The axially disposed ribs are arranged to facilitate stacking of speculums, one over the other, so that the ribs on and inner speculum in the stack will limit the distance the inner speculum can penetrate an outer speculum such that the distal tip of the inner speculum will not come in contact with the distal end membrane or lens of the outer speculum. In addition, the ribs also prevent the tapered inner surface of the outer speculum from coming into locking engagement with the tapered outer surface of the inner speculum which, of course, would make separation of the stacked speculums difficult. The ribs 26, also provide convenient finger gripping surfaces which help facilitate connecting and disconnecting the speculum from a medical thermometer. Additional ribs 30 may be spaced about the body of the speculum which function in the same manner as ribs 26 to attain the same results.

As shown in FIG. 1, three (3) engagement members 22, are disposed at locations that are equally spaced apart from each other around an outer periphery of the proximal end 16 of the speculum 10. When equally spaced apart, each engagement structure 22 is disposed about 120 degrees from its neighbor. In other embodiments, the speculum 10 can include more or less than three engagement members and the engagement structures can be disposed at locations that are not equally spaced about the proximal end of the speculum body.

Figure 2:
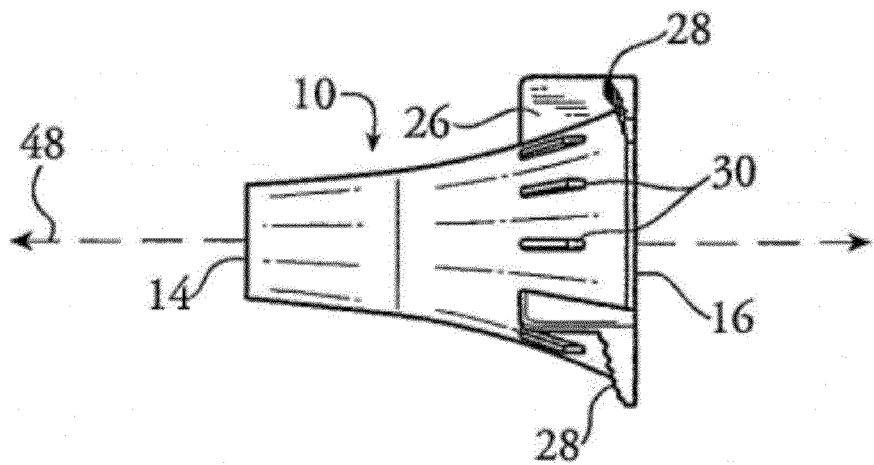
FIG. 2 is a side view of the speculum of FIG. 1.
Figure 3:
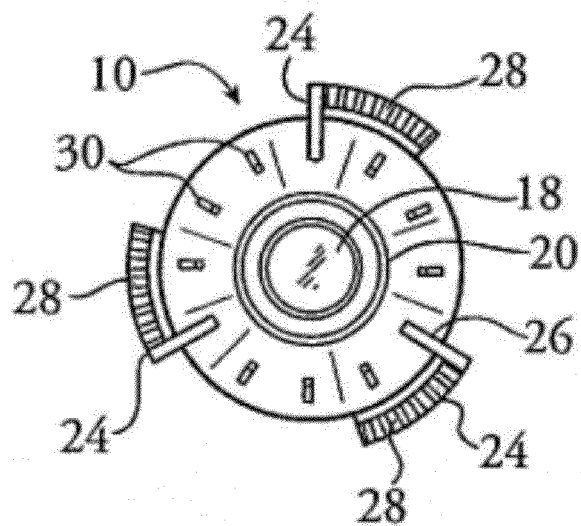
FIG. 3 is a front view of the speculum of FIGS. 1 and 2.
Figure 4:
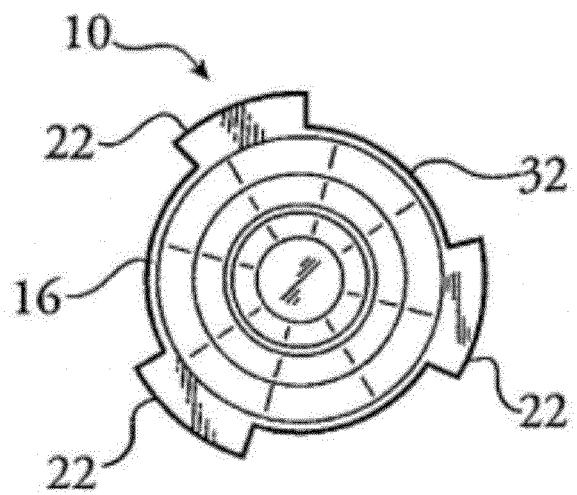
FIG. 4 is a rear view of the speculum of FIGS. 1-3.

FIGS. 2-4 respectively illustrate a side view, front view and rear view of the speculum illustrated in FIG. 1. As shown in FIGS. 1-3, some embodiments include spaced axial ribs 30, also referred to as gripping ribs 30 that are disposed between each of the axial disposed ribs 26 of the engagement members. The ribs 30 also provide further gripping surfaces that can be utilized when attaching the speculum 10 to the medical thermometer 100.

In one aspect of the present invention, a speculum is configured to interoperate with a temperature measuring instrument 100 (See FIG. 13) to provide for a more accurate temperature read out. In this embodiment, the membrane 18 functions to gather thermal energy from the patients ear by conduction and/or radiation and to concentrate the gathered radiation upon the receiving surface of a temperature sensor 124 mounted in the thermometer.

In some embodiments, the membrane 18 is configured simply as an infrared transparent window and function in part, to gather radiation and direct the radiation to the intended target. Reference is made to co-pending U.S. patent application Ser. No. 11/678,657 to Lane, et. al. entitled "Multisite Infrared Thermometer," for further description of this principle.

In some embodiments, the distal aperture 20 can be a simple hole that provides an entrance to a passageway leading to the membrane 18 disposed at a location inside of the body 12. The passageway abuts and is located between the membrane 18 and the outside environment proximate to the distal aperture 20. In some embodiments, an interior surface 32 of the speculum 10 can be configured to improve infrared radiation transmissibility. In some embodiments, the interior surface 32 can be configured to channel thermal energy toward an infrared sensor. In some embodiments, the membrane 18 is manufactured such that it transmits infrared radiation in a manner that provides a consistent source of infrared radiation for an infrared sensor 124 to measure. For example, such a membrane may be comprised of a polyethylene, a polypropylene, starched based polymers, or any other materials that might gather radiation and concentrate it upon a sensor.

A substantially consistent source of infrared radiation enables the infrared sensor 124 to accurately measure a temperature at a specific body site. The properties of the tympanic membrane, such as located within the human ear or within an ear of other types of mammals, inherently provides such a substantially consistent environment in which to measure temperature. Such tympanic probes have found widespread acceptance in the medical industry.

The axilla or armpit can also provide a similarly consistent environment, if the medical practitioner avoids disrupting the thermal equilibrium of the axilla during placement of the medical thermometer 100, and if the effects of ambient infrared radiation and emissivity are accounted for. As stated, the temporal region can provide a substantially consistent source of infrared radiation, but such temporal probes likewise require a fair amount of skill on the part of the medical practitioner and proper conditioning of the temporal site.

In contrast, oral and rectal environments do not provide a substantially consistent source of infrared radiation due to difficulty of access and other conditions from subject to subject.

Figure 5:
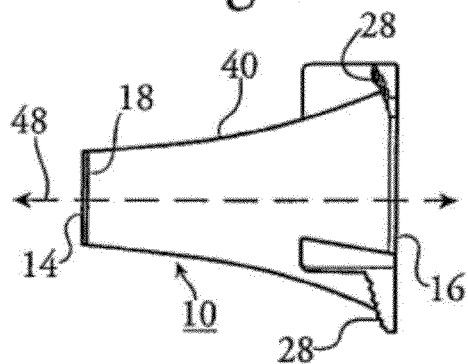
FIG. 5 is a partial cross-section of the speculum of FIGS. 1-3.

FIG. 5 is a partial cross-sectional view of the speculum illustrated in FIGS. 1-3 showing a flat surfaced membrane 18. In some cases, however, a curved membrane may be formed employing known injection molding techniques. This method of manufacture enables the membrane 18 to function as an infrared lens that is configured to gather energy from its surroundings and concentrate the energy upon a target sensor. In use, the curved membrane 18 converges (funnels and directs) incoming infrared radiation toward an infrared sensor 124.

Figure 6A:
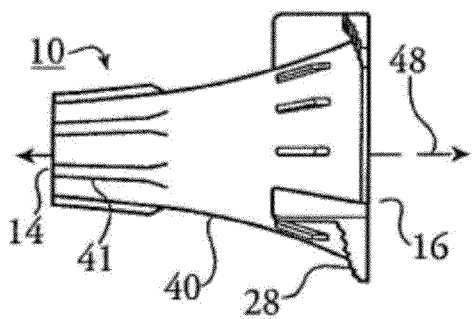
FIG. 6A is a side view of a speculum axially disposed ribs for the removal of cerumen.
Figure 6B:
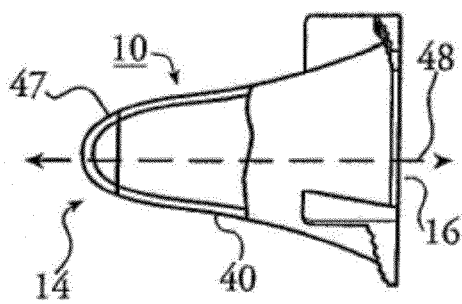
FIG. 6B is a side view in partial section of a speculum that contains a radiation lens for gathering radiation and directing the radiation onto a sensor.
Figure 6E:
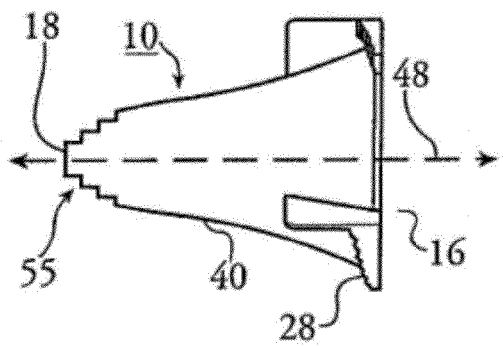
FIG. 6E is a partial side view in section of a speculum containing a double convex radiation lens at the distal end of the speculum body.
Figure 6C:
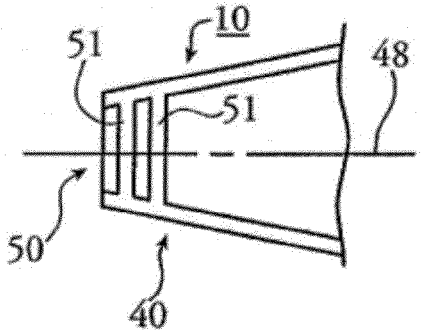
FIG. 6C is a side view of a speculum with a stepped tip membrane.

FIGS. 6A-6C illustrate speculum with various shaped tips. FIG. 6A is a side view of a speculum 10 having a series of spaced apart axially extended ribs 41 for helping to clear cerumen from the ear canal. In this embodiment, the surface topology 41 is formed by alternating ridges and depressions that are located upon the outer surface 40 of the body 12 of the speculum 10. As shown, each ridge and each depression is formed in a direction along a line which is substantially parallel to the axis 48 of the speculum body. Each ridge has top surface and two opposite slopping sides abutting the top surface, which slope in a radial direction substantially towards the axis 48. Each adjacent pair of sloping sides forms a depression, also referred to as a valley, that resides between each pair of neighboring ridges.

Figure 6D:
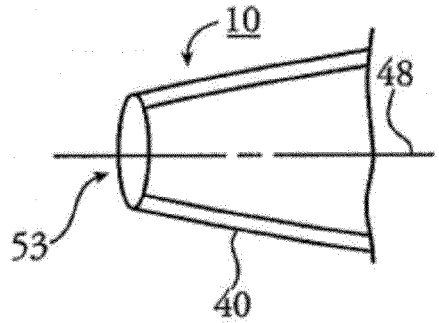
FIG. 6D is a partial side view in section of a speculum showing a radiation lens having multiple elements.

Turning now to FIG. 6B there is illustrated a side view in partial section of a further embodiment of the invention in which a high emissivity radiation lens 47 is positioned in the distal end of the speculum body 40. The lens can be injected molded along with the body of the same infrared transparent material to provide an integrated unit. The lens, in optical terminology is a convex plano element which, as explained above is arranged to gather energy and concentrate the energy upon the surface of an infrared sensor. FIG. 6C is a partial side view in section similar to FIG. 6B in which the lens 50 is made up of a number of elements 51 that are stacked in alignment along the axis 48 of the body 40. FIG. 6D is again a partial side view in section showing the distal end of a speculum body 40 in which a double convex lens 53 is located at the distal end of the speculum body.

FIG. 6E is a side perspective view of an embodiment of a speculum 10 that includes a stepped tip 55. In this embodiment, a membrane 18 is formed at or near the distal end of the spectrum body 40. In other embodiments, a distal aperture 20 may be formed at the most distal step of the stepped tip. As previously described, the distal aperture 20 may be a simple hole that provides an entrance to a passageway leading to a membrane 18 that is disposed at a location inside of the body. The passageway abuts and is located between the membrane 18 and the outside environment proximate to the distal aperture 20. The membrane 18 is generally centered upon the optical axis 48.

Figure 7A:
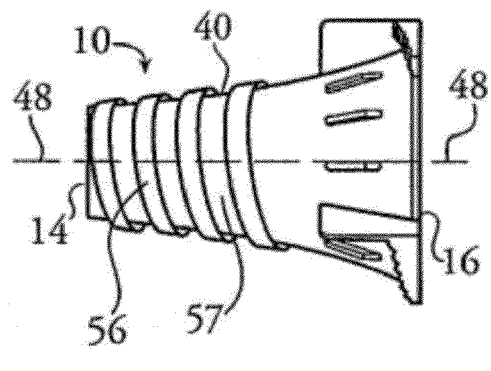
FIG. 7A is a side view of a speculum including a further embodiment of curved channels for the removal of cerumen.
Figure 7B:
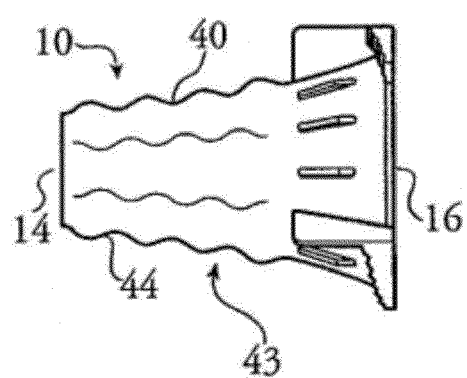
FIG. 7B is a side view of a speculum including a still further embodiment of slot channels for the removal of cerumen.

FIGS. 7A-7B illustrate a side view of another embodiment of a speculum that contain channels for the removal of cerumen. FIG. 7A is a side view of an embodiment of a speculum 10 including a surface topology 42 that includes a spiral thread 56 that is wound about the body of the spectrum. In this embodiment, spiral channel 57 is established between the thread spirals. As shown in FIG. 7A, the spiral thread has a substantially flat upper surface which substantially follows the contour of the speculum body. opposite sides, referred to as sloping sides, that are each substantially perpendicular to the upper side and perpendicular to the optical axis 48. Each adjacent pair of sloping sides forms a side of a depression, also referred to as a valley, that resides between each pair of neighboring ridges. As shown, each depression has a substantially rectangular cross-sectional shape and a flat bottom side.

FIG. 7B is a side view of an embodiment of a speculum 10 including a surface topology 43 for the removal of cerumen (ear wax) from an ear canal. In this embodiment, the surface topology 43 is formed by an arrangement of mounds and depressions, that are formed along the outer surface of the body 12 of the speculum 10. As shown, a plurality of mounds are arranged (located) in a matrix like manner and form rows and columns of mounds. The rows of this matrix are directed substantially perpendicular to, and the columns are directed substantially parallel to, the optical axis 48. Each mound is surrounded by, and each pair of mounds, is separated by, a depression.

As shown, each mound has a curved surface from its lowest (nearest) to its highest (farthest) point relative to the optical axis 48. The adjacent sloping sides of neighboring mounds, forms a depression between those neighboring mounds. Accordingly, each depression has a substantially curved sides along adjacent mounds and has a substantially flat bottom side. A depression (valley) formed between adjacent rows of mounds collectively forms a circumferential depression, also referred to as a circumferential channel 43b.

Figure 8:
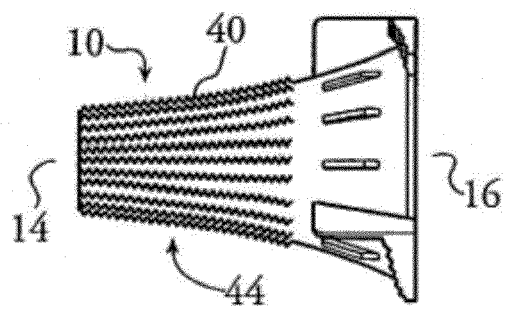
FIG. 8 is a side view of a speculum having a textured exterior surface for the removal of cerumen.

FIG. 8 is a side perspective view of an embodiment of a speculum 10 including a surface topology 44 that is characterized as a textured surface that is configured for the removal of cerumen (ear wax) from an ear canal. In this embodiment, the textured surface includes small randomly disbursed protrusions (or mounds) extending radially away from the exterior surface 40 and the optical axis. This surface topology has substantially similar properties to 100-150 grit of a Mold-Tec texture scale.

The aforementioned and described surface topologies can be plastic injection molded onto an exterior surface 40, comprising a plurality of protrusions, to form a particular surface topology 41-44. Many combinations of the described surface topologies can be employed to remove cerumen from an ear canal.

The membrane 18 acts, at least in part, to gather thermal energy. Where the membrane 18 acts as a receiver of thermal energy, the membrane 18 is disposed near the aperture 20 and thermal energy passes through the distal aperture 20 and heats the membrane 18 via conduction and/or radiation from sources proximate to the membrane and the aperture. The membrane 18 receives thermal energy and in response, the membrane 18 emits infrared radiation that is directed substantially parallel with the optical axis 48, through the cavity 536 within the body 12 of the speculum 10 and towards the infrared sensor 124. The membrane 18 may be comprised of any suitable high emissivity material. As used in this specification, the term "emissivity" is given the same meaning as defined and claimed in U.S. Pat. No. 7,037,083 to O'Neil, the emissivity of membrane 18 may be between 0.9 and 0.95. In some embodiments, the membrane 18 may consist of a metal selected from the group consisting of a metal selected from the group consisting of aluminum, brass, copper, gold or combinations thereof having an emissivity in a range of between 0.8 and 0.95.

Figure 9:
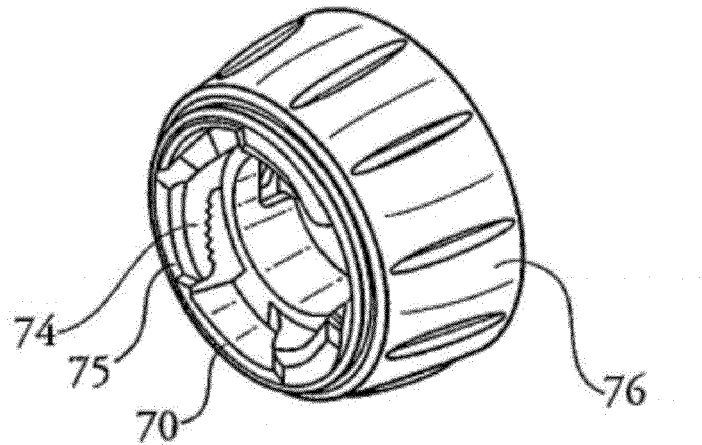
FIG. 9 is a partial front perspective view of a speculum attachment mechanism of a medical thermometer.
Figure 10:
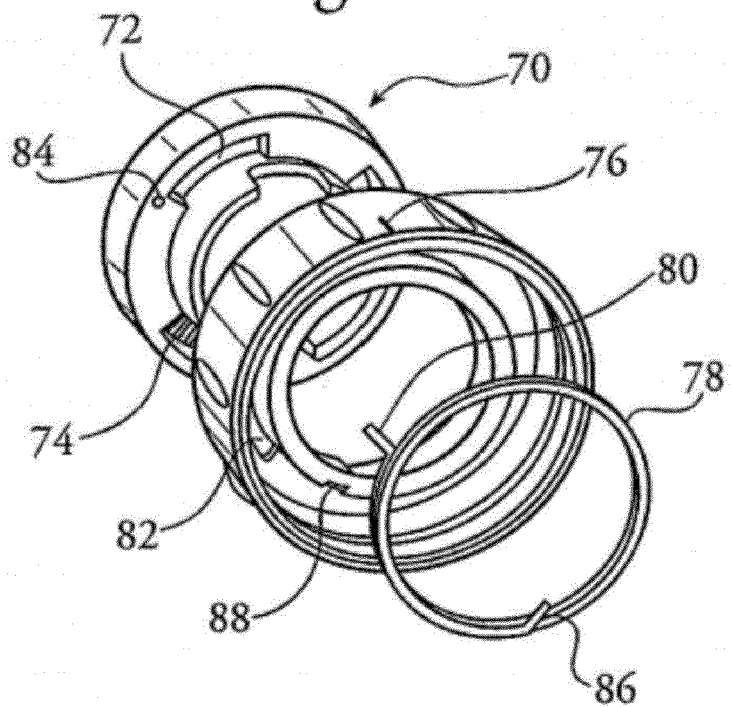
FIG. 10 is an exploded view of the speculum attachment mechanism of FIG. 9.

FIG. 9 is a partial front perspective view and FIG. 10 is an exploded view of a speculum attachment mechanism of a medical thermometer. The speculum attachment mechanism includes a speculum retainer member 70 that is stationarily attached to the distal end of an instrument head 106 (See FIG. 13), the retainer 70 includes a plurality of circumferentially spaced slots 72. In this embodiment, three slots 72, also referred to as securing slots 72, are provided, in which one or more of the slots include circumferential ramped surfaces 74.

As shown in this embodiment, each of the ramped surfaces 74 includes a set of teeth 75 for engaging with the teeth 28 that are provided on the external engagement tabs 22 of the speculum 10 (See FIG. 5). The speculum attachment mechanism further includes a rotatable actuator knob 76 that is biased by means of a spring 78 (See FIG. 10), the spring having an axial first end 80 that passes through a slot in the actuator knob 76 to a hole 84 provided in the retainer member 70. The remaining end 66 of the spring 78 is fitted within a slot 88 that is formed on the actuator knob 76.

FIG. 11 is a first partial front perspective view of a speculum attachment mechanism shown in an operative position while FIG. 12 is a second partial front perspective view (showing teeth) of a speculum. As shown, the retainer member 70 attaches to a front facing surface of the rotatable actuator knob 76, the actuator knob 76 further includes a pin 90 that extends from the front facing surface into that slot 52 within the retainer member 70. Notice that the slot 52 is not configured to have a ramped surface 54 in order to accommodate the pin 90 of the actuator knob 76.

In operation, speculum 10 as described above, is attached onto the distal end of an instrument head 106 of a medical thermometer 100. The speculum 10 is attached so that the circumferential securing portions 24 of each of the external engagement member 22 are inserted into the circumferential slots 72 within the speculum retainer member 70.

In this embodiment, the speculum 10 is turned in a clockwise manner from the perspective of the distal end of the speculum 10 so as to engage the ramped surface and its teeth 28 of the wedge-like engagement features 22 with the corresponding ramped surfaces 74 of the speculum retainer member 70, thereby providing frictional engagement between the teeth 28 and the ramped surface 74 and providing tactile feedback to the user.

In order to release a speculum 10 from the thermometer 100, the actuator knob 76 is rotated in a counter-clockwise direction from the perspective of the distal end of the speculum 10. This causes rotational movement of the knob 56 relative to the stationary speculum retainer member 70 and further causes the front face pin 90 to move within the slot 72 (FIG. 10), driving the speculum 10 rotationally from the slots of the retainer member 70, and releasing the speculum 10 from the attachment mechanism and the thermometer 100.

The design of the herein described speculum 10 can fit a number of other currently existing thermometers, such as those employing bayonet-type attachment schemes and ejector-type mechanisms.

FIG. 13 is a side view of a speculum that is configured to attach to a medical thermometer according to one embodiment of the present invention. As shown, the assembly 100 is comprised of infrared thermometer 104 and speculum 10. The infrared thermometer 104 is similar to prior art infrared thermometers and may be used in an analogous manner. For example, when in use on a patient, speculum 10 is disposed over an infrared sensor 124 with the sensor in close proximity with the radiation lens or membrane. The speculum 10 is then placed at a bodily location for which speculum 10 is specifically configured.

In the embodiment depicted in FIG. 13, speculum 10 is a tympanic probe configured to receive temperature readings from within a patient's ear. Once the probe is suitably disposed within the patient's ear canal, activation button 118 is pressed and a temperature reading is obtained. Within the ear canal, infrared radiation passes through distal aperture 20, the membrane 18, and strikes infrared sensor 124. The infrared sensor 124 generates a signal that corresponds to the amount of infrared radiation received by the infrared sensor 124. This signal is processed by a processor (not shown) in accordance with a set of instructions (e.g. a software program) contained within data storage device 126.

In this manner, a patient's temperature is calculated based upon the aforementioned signal and is thereafter displayed in digital display 120. As would be appreciated by one skilled in the art, a different speculum 10 may require an alternate program to properly calculate a patient's temperature.

The thermometer 100 permits a program to be automatically loaded into the processor dependent upon which speculum 10 is disposed over the infrared sensor 124 and dependent upon which of one or more switches is depressed. In the embodiment depicted in FIG. 13, speculum 10 includes a key for selectively activating one or more switches located on the thermometer. A program is thereafter loaded from data storage device 126 into processor 112. This program contains the instructions necessary for processor 122 to properly calculate the patient's temperature using speculum 10. A speculum having a variation of the design that is shown for speculum 10 may require a different program to properly read the patient's temperature.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

The invention claimed is:

1. A tip element that is securable to a medical thermometer and further includes:
   a conical shaped body having a distal end and an enlarged circular open proximal end;
   a membrane located at the distal end of said body, said membrane being fabricated of a material that gathers infrared energy from its surroundings and concentrates said energy upon a target;
   at least one raised external engageable member that partially encircles the proximal end of said body having teeth, the teeth engaging a co-acting locking mechanism of the medical thermometer;
   said at least one engageable member having a raised rib that is integral therewith and at least partially extends along a direction of said body between the proximal end and the distal end such that said rib is finger engageable for rotating said body about its axis.

2. The tip element of claim 1, wherein said body and said membrane are fabricated of said same material.

3. The tip element of claim 2, wherein said body and said membrane are fabricated of a plastic.

4. The tip element of claim 1, wherein said membrane is fabricated of a material having an emissivity of about between 0.8 and 0.95.

5. A tip element that is securable to a medical thermometer and further includes:
   a conical shaped body having a distal end and an enlarged circular open proximal end;
   a membrane located at the distal end of said body, said membrane being fabricated of a material that gathers infrared energy from its surroundings and concentrates said energy upon a target;
   at least one raised engageable member that partially encircles the proximal end of said body that is adapted to engage a co-acting locking mechanism of the medical thermometer; and
   said at least one engageable member having a raised axial extended rib that is integral therewith such that said rib is finger engageable for rotating said body about its axis,
   wherein said membrane is configured as a plurality of radiation lenses stacked in alignment along the axis of said body for focusing radiation upon a given target,
   wherein said radiation lenses have at least one curved face for concentrating radiation upon a target.

6. A tip element that is securable to a medical thermometer and which further includes:
   an axisymetric shaped body having a distal end and an enlarged circular shaped proximal end that is open;
   at least one raised external engageable member that partially encircles the proximal end of said body having teeth, the teeth engaging a co-acting locking mechanism of the medical thermometer;

said at least one engageable member having a raised rib that is integral therewith and at least partially extends along a direction of said body between the proximal end and the distal end; and said body further includes a section that tapers upwardly from the distal end thereof toward the proximal end and that contains protrusions for removing cerumen from the surface of an ear contacted by said body.

7. The tip element of claim 6, wherein said protrusions include a series of sinusoidal spaced apart waveforms that extend axially along said tapered section.

8. The tip element of claim 6, wherein said protrusions include a plurality of mounds that are randomly disbursed over said tapered section of said body.

9. The tip element of claim 6, wherein said tapered section of said body contain a spiral wound thread that encircles said tapered section.

10. The tip element of claim 6, wherein said protrusions included a series of circumferentially disposed steps that extend rearwardly and upwardly from the distal end of the body.

11. The tip element of claim 6, wherein said protrusions include a plurality of axially extended ribs circumferentially spaced about said tapered section of said body.

12. The tip element of claim 11, wherein each rib has an arcuate shaped top surface, the arc of which is about centered along the axis of the body.

13. The tip element of claim 11, wherein each rib has a flat top surface that is generally parallel with the axis of the body so that each rib blends into the outer wall of the said body.

14. The tip element of claim 8, wherein said mounds are arranged in rows and columns over the outer surface of said tapered section of said body.

15. A tip element that is securable to a medical thermometer and which further includes:

a conical shaped body having a distal end and an enlarged circular shaped open proximal end;

at least one raised external engageable member that partially encircles the proximal end of said body having teeth, the teeth engaging a co-acting locking mechanism of the medical thermometer;

said at least one engageable member having a raised rib that is integral therewith and at least partially extends along a direction of said body between the proximal end and the distal end;

said body further includes a section that tapers uniformly from said distal end of the body towards the proximal end and which contains protrusions for removing cerumen from the surface of an ear that is contacted by said body; and a membrane located at the distal end of said body, said membrane being fabricated of a material that gathers infrared energy from its surroundings and concentrated the energy upon a target.

16. The tip element of claim 15, wherein said membrane is fabricated of a plastic.

17. The tip element of claim 16, wherein said membrane is fabricated of a polypropylene.

18. The tip element of clam 16, wherein said membrane is fabricated of a polyethylene.

19. The tip element of claim 16, wherein said membrane and said body are fabricated of the same material.

20. The tip element of claim 16, wherein said membrane is in the form of a radiation lens having at least one curved surface for directing and focusing radiation onto said target.

\* \* \* \* \*